Aug. 20, 1974 W. H. JESSEL, JR., ET AL Plant Pat. 3,598
CHRYSANTHEMUM PLANT
Filed Feb. 22, 1973
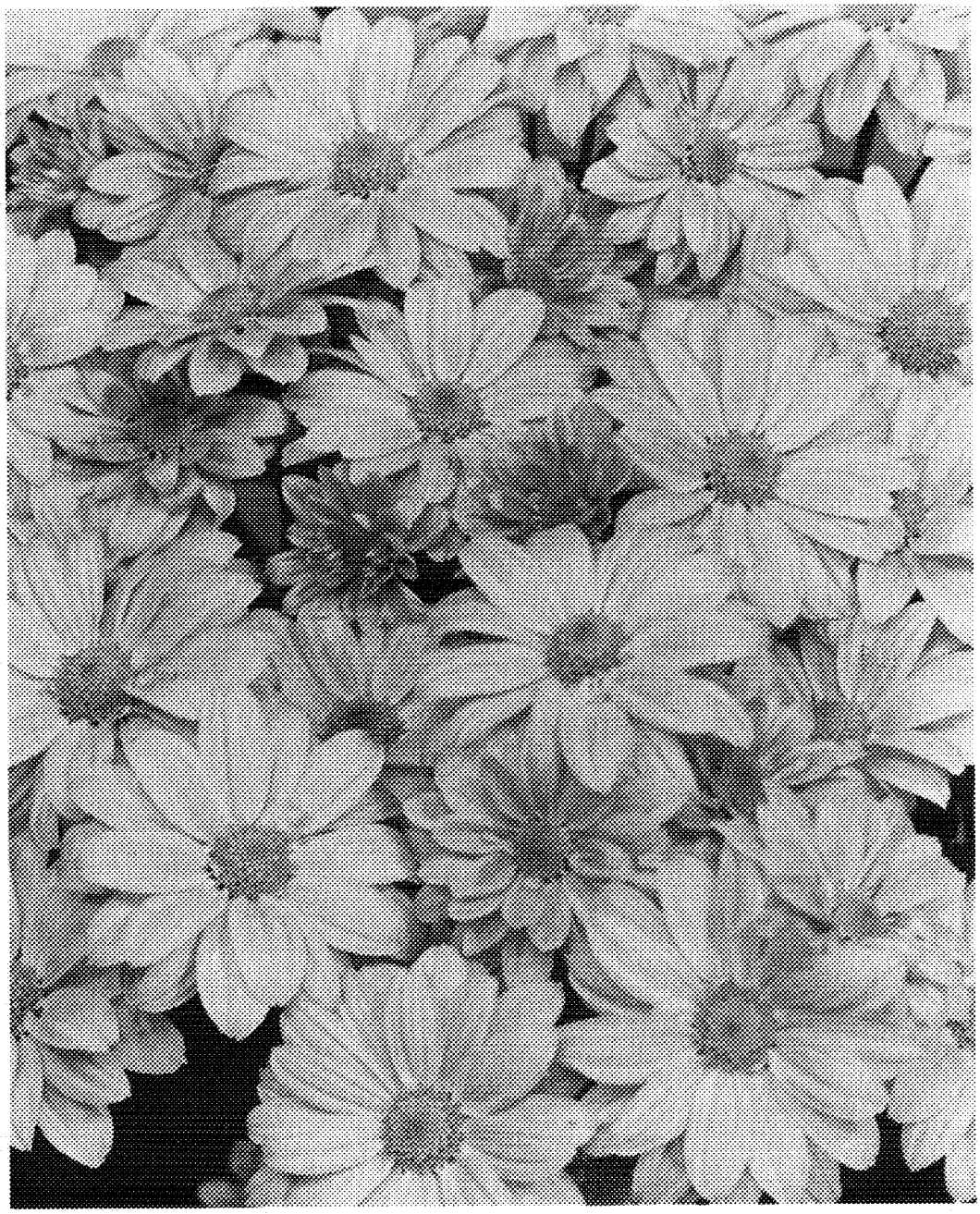

United States Patent Office

Plant Pat. 3,598
Patented Aug. 20, 1974

3,598

CHRYSANTHEMUM PLANT

Walter H. Jessel, Jr., Doylestown, and William E. Duffett, Akron, Ohio, assignors to Yoder Brothers, Inc., Barberton, Ohio

Filed Feb. 22, 1973, Ser. No. 334,737
Int. Cl. A01h *5/00*
U.S. Cl. Plt.—74 1 Claim

The present invention comprises a new and distinct cultivar of chrysanthemum plant known as Wedgewood which is a seedling of Dramatic × Dramatic. The cultivar Dramatic forms the subject matter of U.S. Plant Pat. 3,189.

The new cultivar is unique in the distinguishing features it provides pot mum growers in the chrysanthemum industry, for the following reasons:

1. It can be adapted to commercial pot mum usage with the use of growth regulators and provide a more suitable pot habit than existing pink daisy commercial cultivars.
2. It is suitable as a daisy pot mum, grown as a spray pot, October through June 15 in most northern areas of the United States.
3. It is the first pink daisy pot suitable for winter production as a spray pot in all areas of the United States.
4. It breaks freely from a pinch (4½ to 5 breaks per plant), and develops a high flower count per stem as a spray pot to produce a prolific flowering plant.
5. It has a late 8 to 9½ week response, combined with tall treatment to make it an efficient pot plant to grow. Crop time, depending on season, will range from 10 to 10½ weeks.

The new cultivar was selected from the progeny of the designated cross and when asexually reproduced by cuttings at Barberton, Ohio, has been found to retain its distinctive characteristics through successive propagations.

The new cultivar when grown in the vicinity of Barberton, Ohio, has a response period of approximately 8½ to 9½ weeks, and the following detailed description is based on observations made of the new cultivar in a greenhouse in Barberton, Ohio. The response time, blooming period, color, and total vigor may vary significantly with environmental conditions such as temperature, day length, and light intensity. Suggested flowering in the northern and western United States is October through June as a spray pot. In coastal California, suggested flowering is year round as a spray pot, and April through November as a cut, and in Florida, December through April both as a cut flower spray and as a spray pot.

The accompanying drawing is a color photograph of the new cultivar in pot mum form, with the color being as nearly true as possible with color illustrations of this type.

In the following description, color references are made to the Munsell Color Book, 1963 edition.

Botanical classification: *Chrysanthemum morifolium.*

Bloom:

*Size.*—2¾".
*Fully expanded.*—3¼".
*Borne.*—Clusters on elongated pedicel.
*Stems.*—Strong and wiry.
*Form.*—Daisy (single).
*Permanence.*—12–14 days.
*Color.* (Munsell Color Book). Center of flower—yellow-green, 2.5GY6/6 to yellow, 3.75Y7/12. Base of petals—yellow-green, 2.5GY7/10. Inside of petals—lavender, 7.5P8/4 to light lavender, 7.5P9/2. Reverse of petals—light lavender, 7.5P9/2. Tonality from a distance—light lavender. Discoloration—light lavender, 7.5P9/2.

Petals:

*Texture.*—Smooth.
*Appearance and form.*—Open at base, broad shallow 2-ridged keel, tapering to a 2–5 notched blunt end.
*Arrangement.*—Composite, whorled on a single receptacle.
*Persistence.*—Resist shatter.
*Fragrance.*—Typical chrysanthemum.

Reproductive organs:

*Stamen, anthers.*—200 or more.
*Pollen.*—Abundant to none (functional sterility).
*Arrangement.*—Clustered in center of flower, if present.
*Styles.*—Present both ray and disc florets.
*Length.*—Short.
*Ovaries.*—At the base of petal attached to receptacle.

Plant:

*Form.*—Herbaceous.
*Growth.*—Semi-spreading.
*Height (cut).*—Approximately 32"–35" as a cut spray, given 3 weeks of long days and 12 weeks total crop time as defined in the timetables of Yoder Brothers, Inc., Barberton, Ohio for the various recommended seasons.
*Height (pot).*—Approximately 16"–20" grown in a 5-cutting, 6" pot, grown as a pinched spray pot mum, given 1–2 applications of 2500 p.p.m. B–9 and 9 week tall treatment (1–2 weeks of long days) as defined in the timetables of Yoder Brothers, Inc., Barberton, Ohio, for the various recommended seasons.
*Spread.*—None grown single stem as a cut flower spray. Approximately 12"–16" grown in a 5-cutting, 6" pot, grown as a pinched spray pot mum, given 1–2 applications of 2500 p.p.m. B–9 and 9 week tall treatment (1–2 weeks of long days) as defined in the timetables of Yoder Brothers, Inc., Barberton, Ohio, for the various recommended seasons.

Foliage:

*Top side.*—Dark green, 7.5GY3/4.
*Size.*—4½" long, 2½" wide.
*Quantity.*—Numerous.
*Shape.*—Spatulate lobed.
*Texture.*—Smooth.
*Ribs and veins.*—Prominent.
*Edge.*—Moderately indented.
*Serration.*—Slight.
*Under side.*—Light green, 7.5GY5/4.
*Stipules.*—Prominent.

We claim:

1. A new and distinct cultivar of chrysanthemum characterized particularly as to its uniqueness by its adaptation to commercial pot mum usage with the use of growth regulators to provide a more suitable pot habit than existing pink daisy commercial cultivars; its capability of being grown as a daisy spray pot mum from October through June 15 in most nothern areas of the United States; and by its suitability for winter production as a spray pot in all areas of the United States; by its characteristic of breaking freely from a pinch and developing a high flower count per stem as a spray pot to produce a prolific flowering plant, and by its late 8 to 9½ week response, which, combined with tall treatment, makes it an efficient pot plant to grow.

No references cited.

ROBERT E. BAGWILL, Primary Examiner